(12) United States Patent
Shah et al.

(10) Patent No.: US 7,901,396 B2
(45) Date of Patent: Mar. 8, 2011

(54) TRANSVENOUS MEDICAL DEVICE DELIVERY SYSTEM

(75) Inventors: Sonar Shah, Los Angeles, CA (US); Mark D. Schneider, Mound, MN (US); Brian Raze, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 1266 days.

(21) Appl. No.: 11/380,454

(22) Filed: Apr. 27, 2006

(65) Prior Publication Data

US 2007/0255255 A1 Nov. 1, 2007

(51) Int. Cl.
*A61M 25/00* (2006.01)

(52) U.S. Cl. ........................................ 604/527

(58) Field of Classification Search ............... 604/523, 604/524, 527
See application file for complete search history.

(56) References Cited

U.S. PATENT DOCUMENTS

| 3,485,234 | A | | 12/1969 | Stevens |
| 4,243,050 | A | | 1/1981 | Littleford |
| 5,120,323 | A | | 6/1992 | Shockey et al. |
| 5,964,795 | A | | 10/1999 | McVenes et al. |
| 6,022,336 | A | * | 2/2000 | Zadno-Azizi et al. ... 604/101.05 |
| 6,059,779 | A | | 5/2000 | Mills |
| 6,540,733 | B2 | * | 4/2003 | Constantz et al. ............ 604/507 |
| 6,709,429 | B1 | * | 3/2004 | Schaefer et al. ............. 604/527 |
| 6,733,500 | B2 | | 5/2004 | Kelley et al. |
| 6,755,812 | B2 | | 6/2004 | Peterson et al. |
| 6,836,687 | B2 | | 12/2004 | Kelley et al. |
| 6,871,085 | B2 | | 3/2005 | Sommer |
| 7,297,302 | B2 | * | 11/2007 | Berg et al. ..................... 264/139 |
| 7,438,712 | B2 | * | 10/2008 | Chouinard .................... 604/527 |
| 2003/0130598 | A1 | | 7/2003 | Manning et al. |
| 2003/0144657 | A1 | | 7/2003 | Bowe et al. |
| 2003/0208141 | A1 | | 11/2003 | Worley et al. |
| 2004/0019359 | A1 | | 1/2004 | Worley et al. |
| 2004/0153049 | A1 | * | 8/2004 | Hewitt et al. ................. 604/527 |
| 2004/0215139 | A1 | | 10/2004 | Cohen |
| 2005/0004553 | A1 | * | 1/2005 | Douk ............................ 604/523 |
| 2005/0020914 | A1 | | 1/2005 | Amundson et al. |

FOREIGN PATENT DOCUMENTS

| WO | 2005007228 | 1/2005 |
| WO | WO2005002658 A | 1/2005 |

OTHER PUBLICATIONS

International Search Report, PCT/US2007/066834, Nov. 27, 2007, 6 Pages.

* cited by examiner

*Primary Examiner* — Nicholas D Lucchesi
*Assistant Examiner* — Aarti B Berdichevsky

(57) ABSTRACT

A medical device delivery system and method of manufacture that includes an outer catheter, a first inner catheter insertable through the outer catheter, and a second inner catheter insertable through the first inner catheter and adapted to receive a guidewire extending there through. The first inner catheter includes a braided reinforcement layer and is adapted to receive an elongated medical device extending there through.

19 Claims, 5 Drawing Sheets

TRANSVENOUS MEDICAL DEVICE DELIVERY SYSTEM

TECHNICAL FIELD

The invention relates generally to implantable medical devices and, in particular, to a transvenous delivery system for elongated medical devices.

BACKGROUND

Transvenous endocardial leads may be placed inside a chamber of a patient's heart by passing the lead through a venous entry site, such as the subclavian vein or the cephalic vein, or a tributary thereof, along a venous pathway into the superior vena cava and into the right cardiac chambers. Cardiac vein leads may be advanced further, from the right atrium through the coronary sinus ostium into the coronary sinus and ultimately into one of the various cardiac veins for stimulation and/or sensing of the left heart chambers.

Cardiac lead placement is important in achieving accurate sensing of cardiac signals and proper cardiac stimulation pulse delivery for providing optimal therapeutic benefit from cardiac stimulation therapies such as cardiac resynchronization therapy (CRT). Cardiac vein leads generally need to be small in diameter to allow advancement through the cardiac veins and highly flexible in order to withstand flexing motion caused by the beating heart without fracturing. The small diameter and flexibility of the lead, however, makes advancement of the lead along a tortuous venous pathway challenging. Cardiac vein leads are generally implanted with the aid of a relatively stiff guide catheter and/or guidewire or stylet. Considerable skill and time are required to achieve proper placement of a transvenous lead along a cardiac vein site.

A subselection catheter is a catheter that is relatively smaller in diameter and more flexible than the guide catheter and is used for selecting a cardiac vein branch in which the lead will ultimately be implanted. The guide catheter is typically advanced to the os of the coronary sinus. The subselection catheter is advanced through the guide catheter into the coronary sinus and further into a selected cardiac vein branch with the use of a guidewire. When the targeted implant site is reached, the subselection catheter is removed, and the cardiac vein lead is advanced over the guidewire to the targeted implant site. The guidewire, being very flexible and having a small diameter, sometimes prolapses out of the selected vein branch, back into a larger vessel before the lead is successfully positioned at the targeted implant site. The guidewire then needs to be repositioned, with the use of the subselection catheter. Such occurrences increase the time and difficulty of the implant procedure. Improved transvenous lead delivery systems are needed for facilitating implantation of cardiac leads, particularly for implantation in cardiac vein locations.

DETAILED DESCRIPTION

Figure 1:
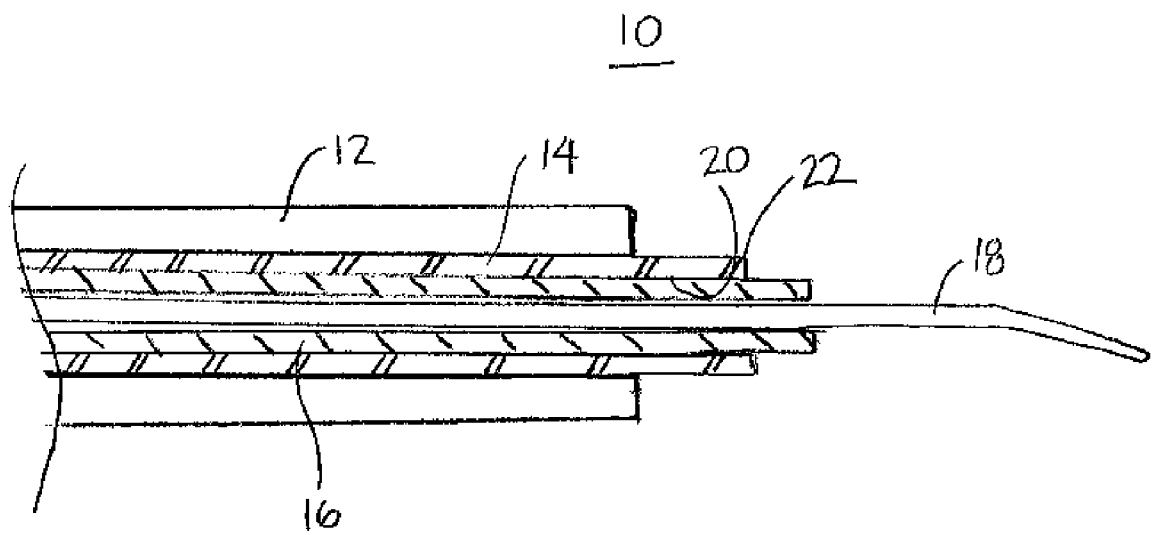
FIG. 1 is a side sectional view of a distal portion of a medical device delivery system according to one embodiment of the invention.

In the following description, references are made to illustrative embodiments for carrying out the invention. It is understood that other embodiments may be utilized without departing from the scope of the invention. For purposes of clarity, the same reference numbers are used in the drawings to identify similar elements. Unless otherwise noted, drawing elements are not drawn to scale.

In one embodiment, the invention is directed to a medical device delivery system used for implanting transvenous cardiac leads in the cardiac venous system, referred to generally as "cardiac vein leads." However, it is recognized that a medical device delivery system provided in accordance with the present invention may be used to deliver other transvenous medical devices, including, for example, fluid delivery devices, diagnostic devices, or sensors.

FIG. 1 is a side sectional view of a distal portion of a medical device delivery system according to one embodiment of the invention. The system includes an outer catheter 12, a first inner catheter 14, and a second inner catheter 16. The first inner catheter 14 is provided as a subselection catheter and a medical device delivery catheter. As such, first inner catheter 14 is provided with an inner diameter 20 adapted to receive an elongated medical device extending there through. The first inner catheter 14 is relatively more flexible than the outer catheter 12 to allow first inner catheter 14 to flexibly track the second inner catheter 16 for subselecting a targeted cardiac vein. The first inner catheter 14 is provided with a reinforcing layer to provide efficient torque transfer from a proximal end that remains outside the patient's body to the distal end 22 being advanced to a targeted implant or therapy site.

In forming first inner catheter 14 with a lumen large enough to pass an elongated medical device, first inner catheter 14 has a lumen too large too closely track a guidewire. As such, second inner catheter 16 is provided to closely track guidewire 18 and provide support to first inner catheter 14 during advancement and rotation.

Second inner catheter 16 is adapted for receiving a guidewire 18 extending there through. Second inner catheter 16 is provided as a flexible, relatively thin-walled sheath for easily tracking guidewire 18. Second inner catheter 16 is arranged telescopically with first inner catheter 14 and outer catheter 12. Second inner catheter 16 is maneuvered in a telescopic manner with first inner catheter 14 until first inner catheter 14 is positioned at a targeted implant or therapy delivery site. For example, during a cardiac vein lead implant procedure, outer catheter 12 is advanced to the os of the coronary sinus. The first and second inner catheters 14 and 16 are advanced into the coronary sinus and, with the use of guidewire 18, advanced in a telescoping manner to sub-select a desired cardiac vein branch. In an alternative embodiment, second inner catheter 16 may be provided as a solid member for supporting first inner catheter 14 and advance in a telescoping manner with first inner catheter 14 to subselect a desired cardiac vein.

Second inner catheter 14 may be provided with a variable durometer having a relatively stiff portion extending from the proximal end, a soft distal portion, and a radio-opaque distal tip. Second inner catheter 14 is typically provided without a reinforcing layer.

Figure 2:
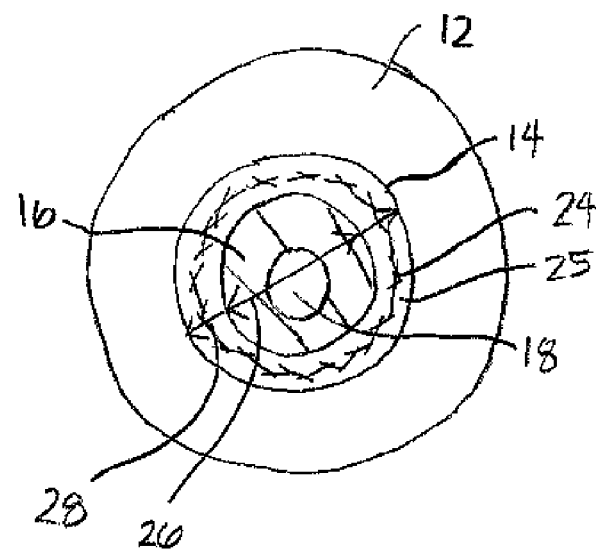
FIG. 2 is an end sectional view of the delivery system shown in FIG. 1.

FIG. 2 is an end sectional view of the delivery system shown in FIG. 1. Outer catheter 12 serves as a guide catheter for first inner catheter 14 and is generally provided as a relatively thicker-walled and/or stiffer catheter than first inner catheter 14. Outer catheter 12 may include a reinforcing layer and provides a lubricious lumen through which first inner catheter 14 is passed. First inner catheter 14 is used to deliver a medical device to an implant site. First inner catheter 14 is provided with an inner diameter 26 large enough to accommodate an elongated medical device. However, the outer diameter 28 of inner catheter 14 is provided small enough to pass through cardiac veins and serve as a sub-selection catheter for selecting a targeted cardiac vein branch. In one embodiment, intended for delivering a 4 French cardiac vein lead, outer catheter 12 is provided with an inner diameter of approximately 7 to 8 French; first inner catheter 14 is provided with an inner diameter of approximately 5 to 6 French, and second inner catheter 16 is provided with an inner diameter of approximately 3 French to accommodate a guide wire. It is to be understood that other catheter dimensions may be used as appropriate for a particular application.

The inner diameter and outer diameter design requirements imposed on first inner catheter 14 for serving as both a sub-selection catheter and a medical device delivery catheter require first inner catheter 14 to be provided with a relatively thin wall. A thin wall also allows first inner catheter 14 to possess lateral or bending flexibility needed to follow a tortuous venous pathway to a targeted cardiac vein branch.

However, first inner catheter 14 is required to possess adequate torsional rigidity to transfer rotational motion between the proximal catheter end and the distal catheter end being advanced to an implant site. First inner catheter 14 includes a reinforcing layer 24, on or in the first inner catheter wall 25, in order to provide an outer diameter small enough to pass through cardiac vein branches, an inner diameter large enough to allow passage of an elongated medical device, and adequate torsional rigidity to allow rotation of the distal catheter end 22 in response to rotation of the proximal catheter end.

Figure 3A:
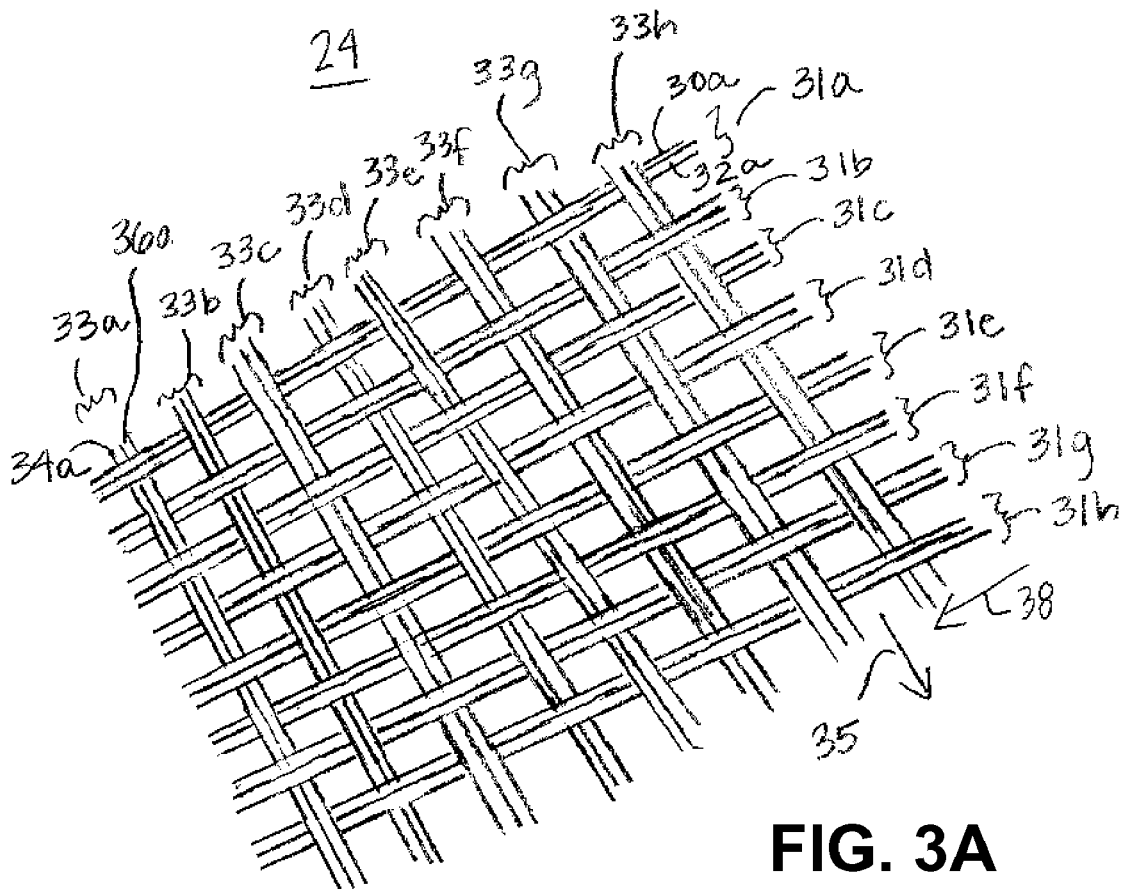
FIG. 3A is an illustration of a braided reinforcing layer according to one embodiment of the invention.

FIG. 3a is an illustration of a braided reinforcing layer according to one embodiment of the invention. Reinforcing layer 24a includes multiple wires braided in pairs or "in tow". In the example shown in FIG. 3a, a first wire 30a is braided in a first braiding direction 38 with a second wire 32a braided in tow with the first wire 30a in the same first braiding direction 38. A third wire 34a is braided in a second braiding direction 35a with a fourth wire 36a braided in tow with the third wire 34a in the same second braiding direction 35. Each wire 30a, 32a, 34a, and 36a may be provided as a single filar or a multifilar wire.

In the example shown eight pairs of wires 31a through 31h are braided in the first braiding direction 38 with eight pairs of wires 33a through 33h braided in the second braiding direction to provide a braided reinforcing layer 24a composed of thirty two wires. Any number of pairs of wires may be braided to from braided reinforcement layer 24 using a braiding machine, such as those commercially available from Steeger, Germany; Wardwel, Mass., or other commercial suppliers. Furthermore, it is recognized that three or more wires may be braided in tow in triplets, quadruplets, etc. By providing multiple wires braided in the "in-tow" manner as shown, the torsional rigidy of first inner catheter 14 is improved, allowing first inner catheter 14 to be manufactured with a thin wall, maneuverable through small cardiac veins and allowing passage of an elongated medical device through first inner catheter 14.

Wires 30a, 32a, 34a, and 36a are typically formed from stainless steel, a shape memory alloy such as Nitinol®, a polymeric fiber such as polyethylene napthalate, or other material that can be formed into a small cross-sectional wire having sufficient tensile strength to undergo the braiding process. The wires 30a, 32a, 34a, and 36a may be provided with a generally round or flat cross-sectional geometry. First inner catheter 14 is provided as a slittable catheter for removing catheter 14 over an implanted medical device. By forming reinforcing layer 24 using a braided polymer wire such as polyethylene napthalate, forces required to slit the catheter body are reduced, making it easier to remove catheter 14 from the implanted medical device without dislodging the medical device from the implant site.

Figure 3B:
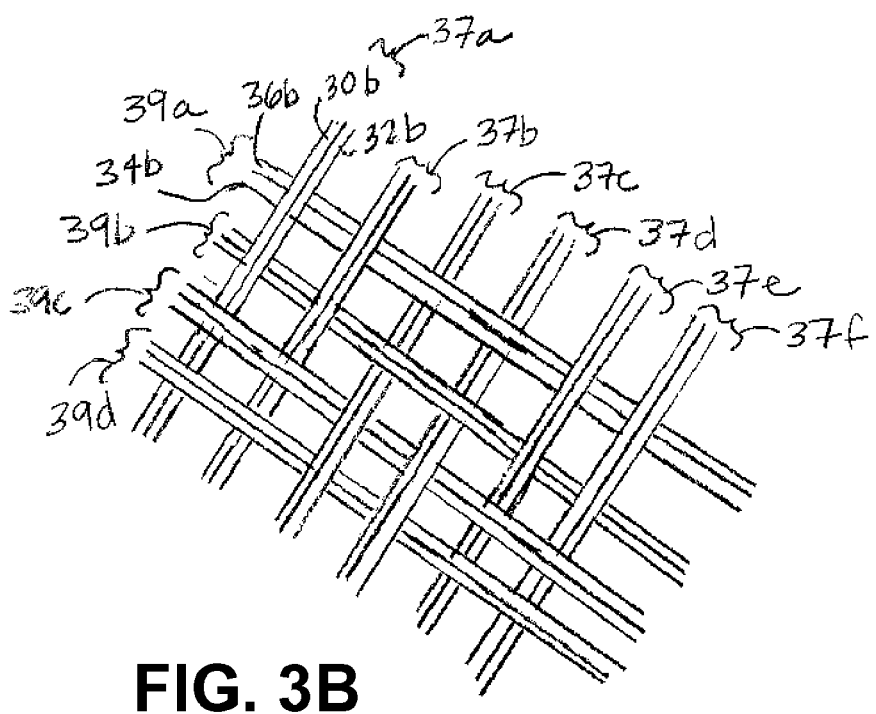
FIG. 3B is an illustration of an alternative braiding pattern.

FIG. 3A illustrates a "one-over-one" tow braiding pattern wherein each wire pair 31a through 31h is braided over one pair of 33a through 33h, then under the next pair of 33a through 33h, and so on. Other tow braiding patterns are possible. For example, a "two-over-two" tow braiding pattern is illustrated in FIG. 3B. Each wire pair 37a through 37f is braided over two pairs of 39a through 39d, then under the next two pairs of 39a through 39d, and so on. It is further recognized that while the tow braiding patterns shown in FIGS. 3A and 3B represent a substantially constant pic rate, reinforcing layer 24 may be provided with a variable pic rate, imparting variable pushability and flexibility along the length of the first inner catheter.

Figure 4:
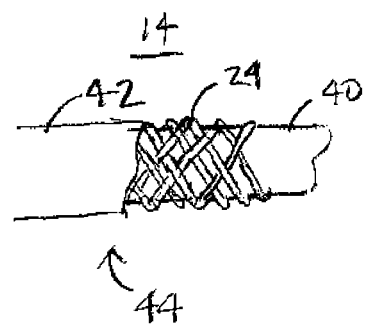
FIG. 4 is a cut-away view of a first inner catheter having a braided reinforcing layer.

FIG. 4 is a cut-away view of a first inner catheter having a braided reinforcing layer. First inner catheter 14 includes an elongated shaft 44 typically constructed using an inner tubular member 40 defining the inner lumen of catheter 14 through which the second inner catheter extends and an elongated medical device is passed. Inner tubular member 40 may be formed from a fluoropolymer such as polytetrafluoroethylene (PTFE), a polyamide such as nylon, a polyolefin, a polyimide, or other materials which provide a generally lubricious inner lumen for passing the second inner catheter and through which an elongated medical device.

Braided reinforcing layer 24 is formed over the outer surface of the inner tubular member 40. The braid density or "pic count" may be constant or variable and will be selected to provide the desired lateral flexibility, torsional rigidity, kink resistance, and pushability needed for a particular application. The pic count will typically range from 20 to 150 pics/inch and will usually fall in the range of approximately 45-60 pics/inch. An outer tubular member 42 is formed over braided reinforcing layer 24. Outer tubular member 42 is typically formed of a soft thermoplastic material such as a polyamide polyether block polymer, polyurethanes, silicone rubbers, nylons, polyethylenes, or fluoronated hydrocarbon polymers.

First inner catheter 14 may be provided having variable mechanical properties along the length of the catheter shaft 44. For example, catheter shaft 44 may be provided with three distinct regions as generally disclosed in U.S. Pat. No. 5,676, 659 (McGurk), hereby incorporated herein by reference in its entirety. A first region extending from the proximal end of first inner catheter 14 includes outer tubular member 42, reinforcing layer 24 and inner tubular member 40. A second region extends from the termination of reinforcing layer 24 and includes inner and outer tubular members 40 and 42. The second region serves as a transition region between the first region and a third region including only outer tubular member 42. Outer tubular member 42 is formed to provide a continuous inner diameter with the inner tubular member 40 to thereby provide a constant diameter medical device delivery lumen. First inner catheter 14 may be provided with a distal end formed of a radio-opaque material.

Figure 5:
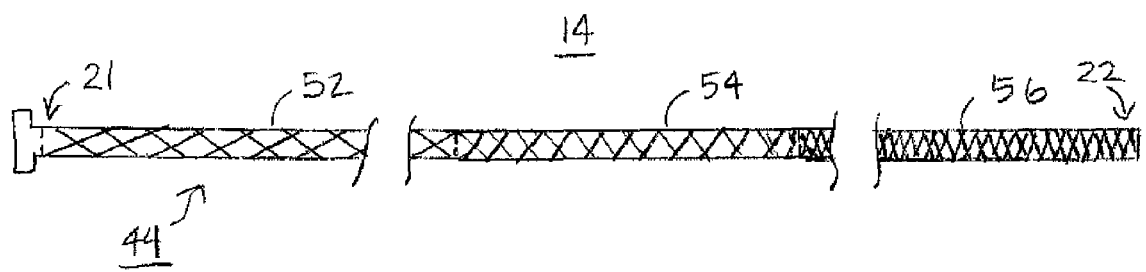
FIG. 5 is a plan view of the first inner catheter according to one embodiment.

FIG. 5 is a plan view of one embodiment of first inner catheter 14 formed with a braided layer having a variable pic count. In addition or alternatively to selecting different materials for the inner and outer tubular members for forming inner catheter 14 with variable mechanical properties along shaft 44, the reinforcing layer may be braided with a variable pic count. Shaft 44 is shown having three regions 52, 54 and 56. Proximal region 52 extends distally from proximal end 21. Distal region 56 extends proximally from distal end 22. Region 54 is a transition region extending between region 52 and 54.

The reinforcing layer formed along proximal region 52 is provided with a low pic count, which results in a relatively more axial orientation of the wires forming the reinforcing layer giving proximal region 52 enhanced pushability. The pic count is gradually transitioned from a lower pic count to a higher pic count along transition region 54. Distal region 56 is provided with a higher pic count than proximal region 52, giving distal region 56 enhanced flexibility. It is recognized that multiple regions may be formed having varying pic counts to provide shaft 44 with desired variation in mechanical properties.

Figure 6:
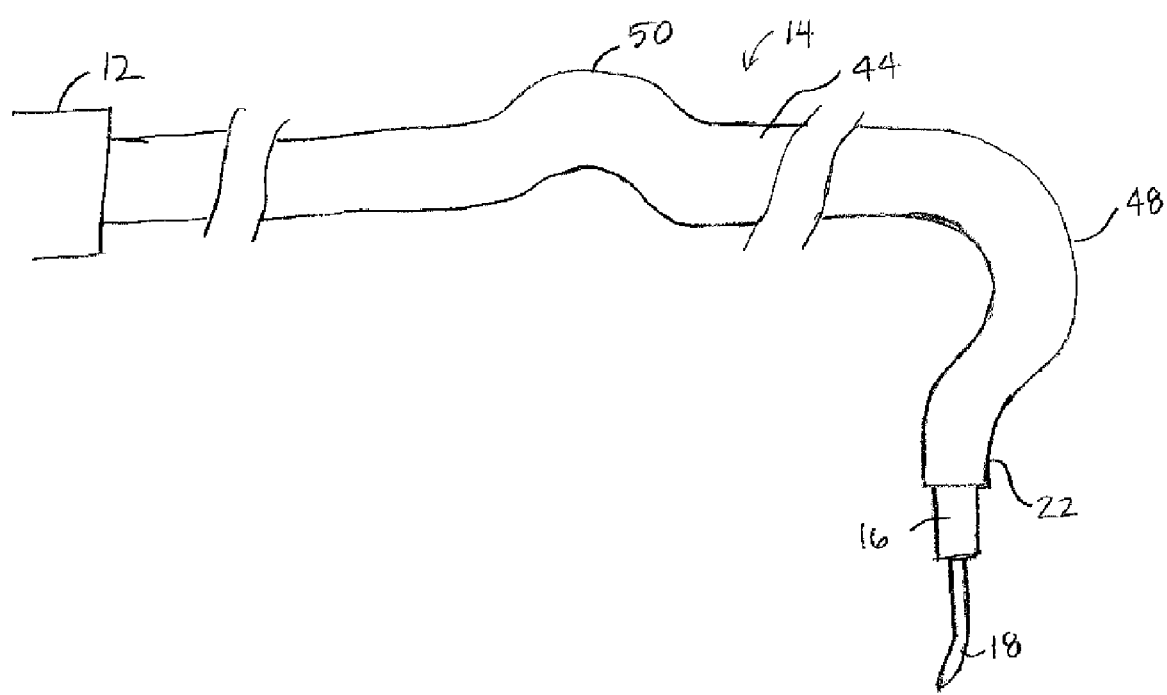
FIG. 6 is a distal plan view of a medical device delivery system according to another embodiment of the invention.

FIG. 6 is a distal plan view of a delivery system according to another embodiment of the invention. First inner catheter 14 may be provided with a pre-shaped distal portion 48 including one or more curves, bends or angles arranged proximate distal end 22 to facilitate subselection of a targeted cardiac vein. In the example shown, first inner catheter 14 is provided with a pre-shaped distal end corresponding to an Amplatz curve. The curved shape will be straightened by inserting second inner catheter 16 through first inner catheter 14. Second inner catheter 16 is formed as a thin sheath that tracks guidewire 18 and provides mechanical support to first inner catheter 14 during advancement and rotation of first inner catheter 14. Second inner catheter 16 may be retracted into first inner catheter 14 to allow pre-shaped distal end 22 to conform to its natural bias for vein subselection.

In some embodiments, first inner catheter 14 may additionally include a second pre-shaped portion 50 along first inner catheter shaft 44, proximal to the distal pre-shaped portion 48. Proximal pre-shaped portion 50 may be provided as a generally "C-shaped" curve or other pre-shaped bend, curve, or angle. Proximal pre-shaped portion 50 is formed for providing cardiac vein wall support when tracking into a cardiac vein branch.

Figure 7:
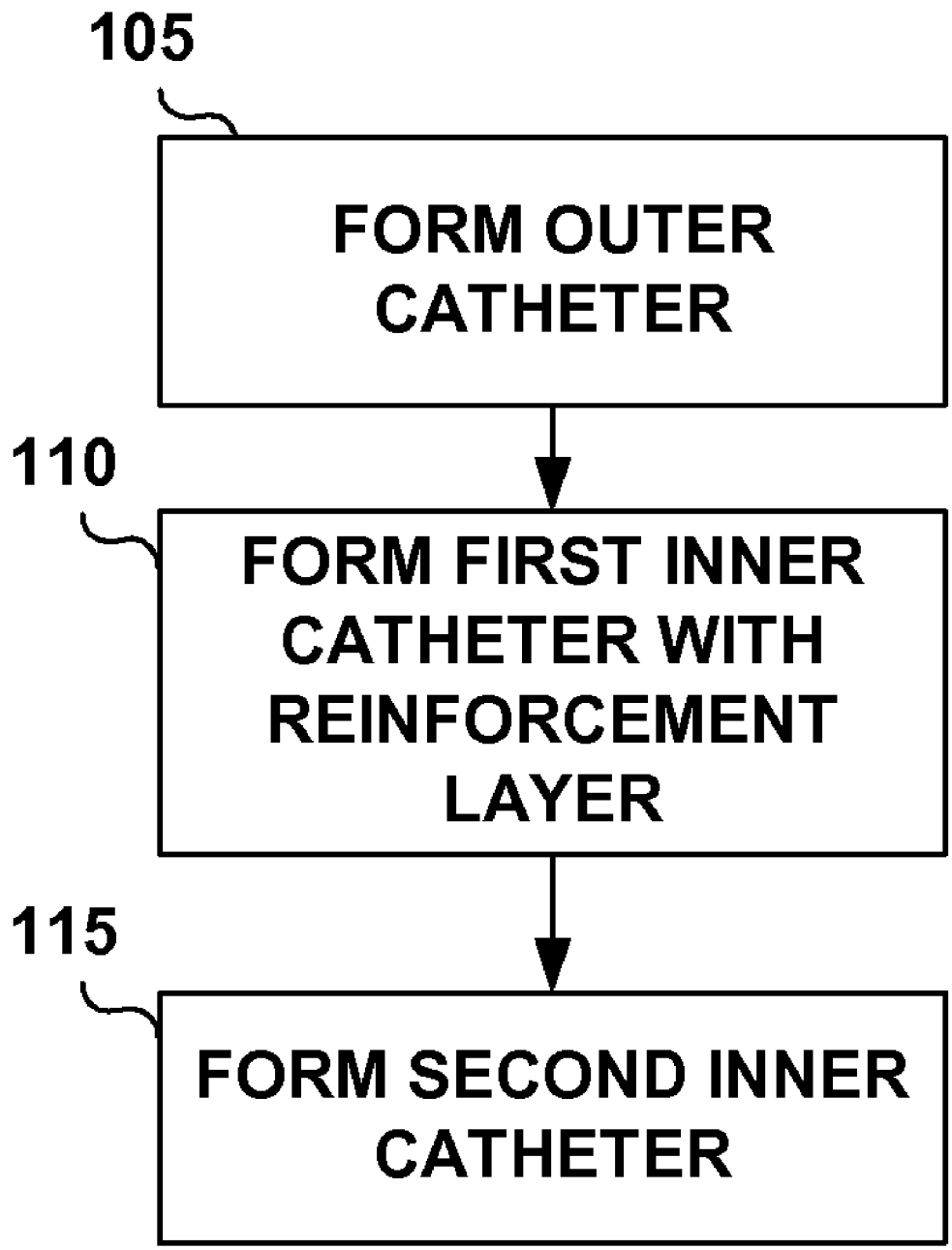
FIG. 7 is a flow chart summarizing a method for fabricating a medical device delivery system.

FIG. 7 is a flow chart summarizing a method for manufacturing a medical device delivery system. At block 105 the outer catheter is formed. The outer catheter may be formed with or without a reinforcing layer and with or without a pre-curved or other pre-shaped distal end. At block 110, the first inner catheter is formed as a thin-walled catheter having a reinforcing layer and is sized to pass through the outer catheter and allow passage of an elongated medical device through the first inner catheter lumen. The reinforcing layer is formed by applying a plurality of multifilar or single filar wires in an "in tow" braiding pattern on or incorporated in the first inner catheter wall. The first inner catheter may be formed with a pre-curved or other pre-shaped distal portion and/or proximal portion of the catheter shaft. The second inner catheter is formed at block 115 and is sized to pass through the first inner catheter.

Thus, a medical device delivery system has been presented in the foregoing description with reference to specific embodiments. It is appreciated that various modifications to the referenced embodiments may be made without departing from the scope of the invention as set forth in the following claims.

The invention claimed is:

1. A medical device delivery system, comprising:
   an outer catheter;
   a first inner catheter insertable through the outer catheter, the first inner catheter adapted to receive an elongated medical device extending therethrough;
   a braided reinforcement layer positioned within the first inner catheter that includes a plurality of wires, wherein a first wire of the plurality of wires is braided in tow with a second wire of the plurality of wires in a first braiding direction, and a third wire of the plurality of wires is braided in tow with a fourth wire of the plurality of wires in a second braiding direction, the braided reinforcement layer having a length extending over the length of the first inner catheter; and
   a second inner catheter insertable through the first inner catheter and adapted to receive a guidewire extending therethrough.

2. The system of claim 1 wherein the first inner catheter includes an inner tubular member and an outer tubular member, and the braided reinforcement layer is disposed between the inner and outer tubular members.

3. The system of claim 1 wherein each of the first, second, third and fourth wires are multifilar wires.

4. The system of claim 1 wherein the braided reinforcement layer includes wires formed from one of stainless steel and polyethylene napthalate.

5. The system of claim 1 wherein the first and second wires are braided with the third and fourth wires in one of a one-over-one pattern and a two-over-two pattern.

6. The system of claim 1 wherein the plurality of wires includes eight pairs of wires braided in the first direction and eight pairs of wires braided in the second direction.

7. The system of claim 1 wherein the second inner catheter includes a variable durometer catheter body.

8. The system of claim 1 wherein the first inner catheter includes a distal catheter end and a pre-shaped portion spaced proximally from the distal catheter end.

9. The system of claim 1 wherein the first inner catheter is provided with an inner diameter of approximately 5.8 French and an outer diameter of approximately 7 French.

10. A method for manufacturing a medical device delivery system, comprising:
    forming an outer catheter;
    forming a first inner catheter insertable through the outer catheter and adapted to receive an elongated medical device extending therethrough wherein forming the first inner catheter includes forming a braided reinforcement layer including a first wire braided in tow with a second wire in a first braiding direction and a third wire braided in tow with a fourth wire in a second braiding direction; and
    forming a second inner catheter insertable through the first inner catheter adapted to receive a guidewire extending therethrough.

11. The method of claim 10 wherein forming the first inner catheter includes forming an inner tubular member, disposing the braided reinforcement layer over an outer surface of the inner tubular member, and forming an outer tubular member over the braided reinforcement layer.

12. The method of claim 10 wherein each of the plurality of wires is a multifilar wire.

13. The method of claim 10 wherein the braided reinforcement layer includes wires formed from any of stainless steel and polyethylene napthalate.

14. The method of claim 10 wherein the plurality of wires includes eight pairs of wires braided in the first direction and eight pairs of wires braided in the second direction.

15. The method of claim 10 wherein forming the second inner catheter includes forming a second inner tubular body having a variable durometer.

16. The method of claim 10 wherein forming the first inner catheter includes forming a first pre-shaped portion proximate a distal catheter end.

17. The method of claim 10 wherein the first inner catheter is formed with an inner diameter of approximately 5.8 French and an outer diameter of approximately 7 French.

18. The method of claim 10 wherein the first and second wires are braided with the third and fourth wires in one of a one-over-one pattern and a two-over-two pattern.

19. The method of claim 18 wherein forming the first inner catheter includes forming a second pre-shaped portion spaced proximally from the first pre-shaped portion.

* * * * *